(12) United States Patent
Osterwise et al.

(10) Patent No.: US 10,587,626 B2
(45) Date of Patent: *Mar. 10, 2020

(54) UNIVERSAL SUBSCRIBER IDENTITY RECOGNITION AND DATA CLASSIFICATION

(71) Applicant: AT&T MOBILITY II LLC, Atlanta, GA (US)

(72) Inventors: Robert Osterwise, Cumming, GA (US); Brian Greaves, Atlanta, GA (US); Stephen T. Hardin, Suwanee, GA (US); Erie Lai Har Lau, Redmond, WA (US)

(73) Assignee: AT&T MOBILITY II LLC, Atlanta, GA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/038,856

(22) Filed: Jul. 18, 2018

(65) Prior Publication Data
US 2018/0324189 A1 Nov. 8, 2018

Related U.S. Application Data

(63) Continuation of application No. 14/969,560, filed on Dec. 15, 2015, now Pat. No. 10,057,272.

(51) Int. Cl.
*H04L 29/06* (2006.01)
*G06F 21/78* (2013.01)
(Continued)

(52) U.S. Cl.
CPC ............ *H04L 63/105* (2013.01); *G06F 19/00* (2013.01); *G06F 21/10* (2013.01); *G06F 21/78* (2013.01);
(Continued)

(58) Field of Classification Search
CPC . H04L 63/105; H04L 63/0442; H04L 69/324; G16H 10/60; H04W 4/80; G06F 19/00; G06F 21/10; G06F 21/78
See application file for complete search history.

(56) References Cited

U.S. PATENT DOCUMENTS

2006/0036755 A1* 2/2006 Abdullah ................ H04L 67/34
709/230
2007/0287416 A1* 12/2007 Ku ........................ H04M 15/00
455/406
(Continued)

*Primary Examiner* — Yonas A Bayou
(74) *Attorney, Agent, or Firm* — Cantor Colburn LLP (57) ABSTRACT

An aspect includes storing data elements in a storage space of a memory device. The storage space is allocated for an account of a subscriber of a universal subscriber identification system. An aspect also includes assigning subscriber-inputted security levels to the data elements. The security levels define varying degrees of access protections associated with the data elements. An aspect further includes generating a security envelope that includes a data element selected from the storage space. The security envelope is configured with an access protection scheme that is commensurate with a corresponding assigned security level. An aspect also includes providing access to the selected data element by another subscriber of the universal subscriber identification system via the security envelope. The access is provided in accordance with the access protection scheme.

18 Claims, 6 Drawing Sheets

(51) Int. Cl.
*H04W 4/80* (2018.01)
*H04L 29/08* (2006.01)
*G16H 10/60* (2018.01)
*G06F 21/10* (2013.01)
*G06F 19/00* (2018.01)
*H04W 88/02* (2009.01)

(52) U.S. Cl.
CPC ......... *G16H 10/60* (2018.01); *H04L 63/0442* (2013.01); *H04L 69/324* (2013.01); *H04W 4/80* (2018.02); *G06F 2221/2113* (2013.01); *H04W 88/02* (2013.01)

(56) References Cited

U.S. PATENT DOCUMENTS

| | | | | |
|---|---|---|---|---|
| 2008/0319799 | A1* | 12/2008 | Knowlton | G06Q 50/24 |
| | | | | 705/3 |
| 2009/0287589 | A1* | 11/2009 | Fivel | G06Q 10/087 |
| | | | | 705/28 |
| 2012/0184212 | A1* | 7/2012 | Kim | H04W 52/0229 |
| | | | | 455/41.2 |
| 2012/0304290 | A1* | 11/2012 | McPhail | H04L 63/101 |
| | | | | 726/22 |
| 2013/0054611 | A1* | 2/2013 | Lee | G06F 21/6227 |
| | | | | 707/741 |
| 2015/0072616 | A1* | 3/2015 | Rong | H04W 8/183 |
| | | | | 455/41.1 |
| 2015/0119015 | A1* | 4/2015 | Gai | H04W 8/005 |
| | | | | 455/418 |
| 2015/0120329 | A1* | 4/2015 | Rangadass | G06F 19/321 |
| | | | | 705/3 |
| 2015/0242629 | A1* | 8/2015 | Lindo | G06F 21/53 |
| | | | | 726/1 |
| 2015/0271677 | A1* | 9/2015 | Van Nieuwenhuyze | |
| | | | | H04W 12/08 |
| | | | | 455/41.1 |
| 2015/0350251 | A1* | 12/2015 | Brander | H04L 63/20 |
| | | | | 713/168 |

* cited by examiner

UNIVERSAL SUBSCRIBER IDENTITY RECOGNITION AND DATA CLASSIFICATION

This application is a continuation of U.S. Non-Provisional application Ser. No. 14/969,560, entitled "UNIVERSAL SUBSCRIBER IDENTITY RECOGNITION AND DATA CLASSIFICATION", filed Dec. 15, 2015, the contents of which are incorporated herein by reference in its entirety.

BACKGROUND

The present disclosure relates generally to information security, and more particularly, to universal subscriber identity recognition and data classification.

Consumers have multiple identities. In an Internet-of-Things (IoT) world, the number of these identities is likely to increase. These identities may come in the form of personal identification or access to a social network, subscriptions in a security model network, a mobile phone number in a wireless network or email address and contact details in a WAN, and recipients or sources of data elements. Other identities may include a boarding pass in a transit transaction, a user ID to access a building, a patient identification in a health care system, password access to a secure network, and machine-to-machine communication from a sending device to a receiving device and vice-versa.

BRIEF SUMMARY

Exemplary embodiments include a method for universal subscriber identity recognition and data classification. The method includes storing data elements in a storage space of a memory device. The storage space is allocated for an account of a subscriber of a universal subscriber identification system. The method also includes assigning, via a computer processor, subscriber-inputted security levels to the data elements. The security levels define varying degrees of access protections associated with the data elements. The method further includes generating, via the computer processor, a security envelope that includes a data element selected from the storage space. The security envelope is configured with an access protection scheme that is commensurate with a corresponding assigned security level. The method also includes providing access to the selected data element by another subscriber of the universal subscriber identification system via the security envelope. The access is provided in accordance with the access protection scheme Other exemplary embodiments include an apparatus and a computer program product for universal subscriber identity recognition and data classification.

Other systems, methods, and/or computer program products according to embodiments will be or become apparent to one with skill in the art upon review of the following drawings and detailed description. It is intended that all such additional systems, methods, and/or computer program products be included within this description, be within the scope of the exemplary embodiments, and be protected by the accompanying claims.

BRIEF DESCRIPTION OF DRAWINGS

Referring now to the drawings wherein like elements are numbered alike in the several FIGURES.

The detailed description explains the exemplary embodiments, together with advantages and features, by way of example with reference to the drawings.

DETAILED DESCRIPTION OF EMBODIMENTS

Embodiments provide universal subscriber identity recognition and data classification (also referred to herein as universal subscriber identification service). The embodiments identify a set of universal recognition and classification for individuals or subscribers, their data, and the permissive access requirements to share these data elements. A subscriber may able to classify data with varying levels of security protection.

Figure 1:
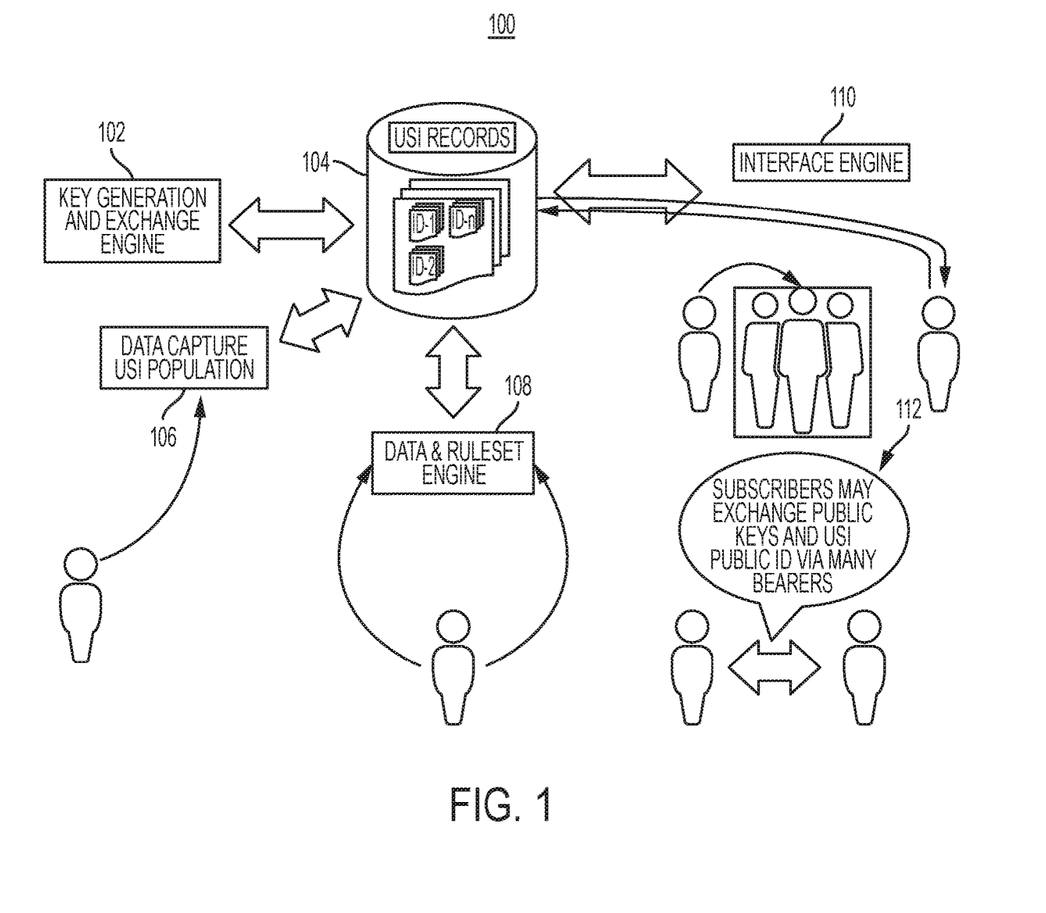
FIG. 1 illustrates a component architecture for use in implementing universal subscriber identity recognition and data classification according to an embodiment.

Turning now to FIG. 1, component architecture and data flow diagram 100 for implementing universal subscriber identification (USI) service will now be described in an embodiment. Diagram 100 includes a key generation and exchange engine 102, a database 104 storing subscriber records, and a data capture component 106. The key generation and exchange engine 102 and the data capture component 106 are each communicatively coupled to the database 104. In an embodiment, the key generation and exchange engine 102 resides on a network device, such as a network server computer, mainframe computer, or other computing device that is configured to generate and disseminate public and private keys used in facilitating the universal subscriber identification service described herein. The key generation and exchange engine 102 is configured to create public and private keys for each subscriber of the universal subscriber identification service. Once a subscriber registers for the universal subscriber identification service, a record is created for the subscriber and stored in the database 104. The subscriber and subscriber record are identifiable by an assigned public identifier that is accessible to other subscribers and/or the general public. Individuals, such as other subscribers, can access data elements of the subscriber that are considered public information, based on public settings assigned to the public data elements by the subscriber. For example, a public data element may be the subscriber's name. The subscriber records may store the keys generated by the engine 102.

The data capture component 106 receives various types of data elements corresponding to subscribers of the universal subscriber identification service. The data elements may include any information that the subscriber wishes to retain and/or protect from unintended exposure to other individuals or entities. A model 300 illustrating sample data elements corresponding to a subscriber is shown and described in FIG. 3. The data elements can be uploaded or transmitted directly from the subscriber or from other authorized entities. In an embodiment, the data capture component 106 resides on a communications device of the subscriber. The communications device can be one of many different devices associated with the subscriber. For example, the communications device can be a personal computer, laptop, tablet, smart phone, or personal digital assistant. In addition, other communications devices can be employed by the subscriber in providing data elements to the database 104. For example, in an Internet-of-Things (IoT) environment, communications devices can include vehicle control system devices, home appliances, home and business security network devices, etc. The data capture component 106 captures and/or receives the data elements and transmits the data elements for storage in the database 104. Until these data elements are classified with security assignments by the subscriber, the data elements are not accessible to anyone but the subscriber. These features are described further herein.

Also included in the component architecture 100 is a data and rule set engine 108 and an interface engine 110, each of which is communicatively coupled to the database 104. In an embodiment, the data and rule set engine 108 is configured to enable a subscriber to assign security levels to each of the data elements. Each of the security levels defines an access protection scheme that is applied to the data elements based on a level of protection desired by the subscriber. For example, in one embodiment, the security levels can include public, private, and confidential, in which data elements having a 'public' security level are freely accessible to other subscribers and/or the public in general; data elements having a 'private' security level are given moderate access protection through a corresponding access protection scheme; and data elements having a 'confidential' security level are given the greatest level of access protection available through a corresponding access protection scheme.

In an embodiment, a common, shared public key may be assigned to every subscriber of the universal subscriber identification service, such that once a subscriber posts or shares a data element using his/her private key, any subscriber having the shared public key may access the data element. In addition, the subscriber may decide to share a data element 'on demand' with a subscriber who may not have the shared public key (or a non-subscriber who does not possess the public key), in which the target recipient of the data element submits a request for the data element, and the subscriber authorizes the sharing of the data element at the time of the request. In this embodiment, the data element may be shared with the recipient along with the subscriber's public key. Thus, the data and rule set engine 108 enables the subscriber to define what information the subscriber is willing to share, with whom the subscriber is willing to share, and under what conditions the subscriber is willing to share.

In an embodiment, the subscriber may pre-package certain data elements via the data and rule set engine 108 in advance of sharing the information. In addition, the subscriber may re-classify the data elements, and/or modify assigned security levels through the data and rule set engine 108.

The interface engine 110 is configured to enable the subscriber to share selected data elements regulated by the security settings. This feature is shown and described further in FIGS. 5 and 6.

In an embodiment, the key generation and exchange engine 102, the data capture component 106, the data and rule set engine 108, and interface engine 110 may be implemented, at least in part, at an end user device, such as a computing device of a subscriber of the universal subscriber identification service. In another embodiment, one or more of the key generation and exchange engine 102, database 104, data capture component 106, data and rule set engine 108, and interface engine 110 may be implemented by a server computer in a client/server network, or a cloud computing network.

Figure 2:
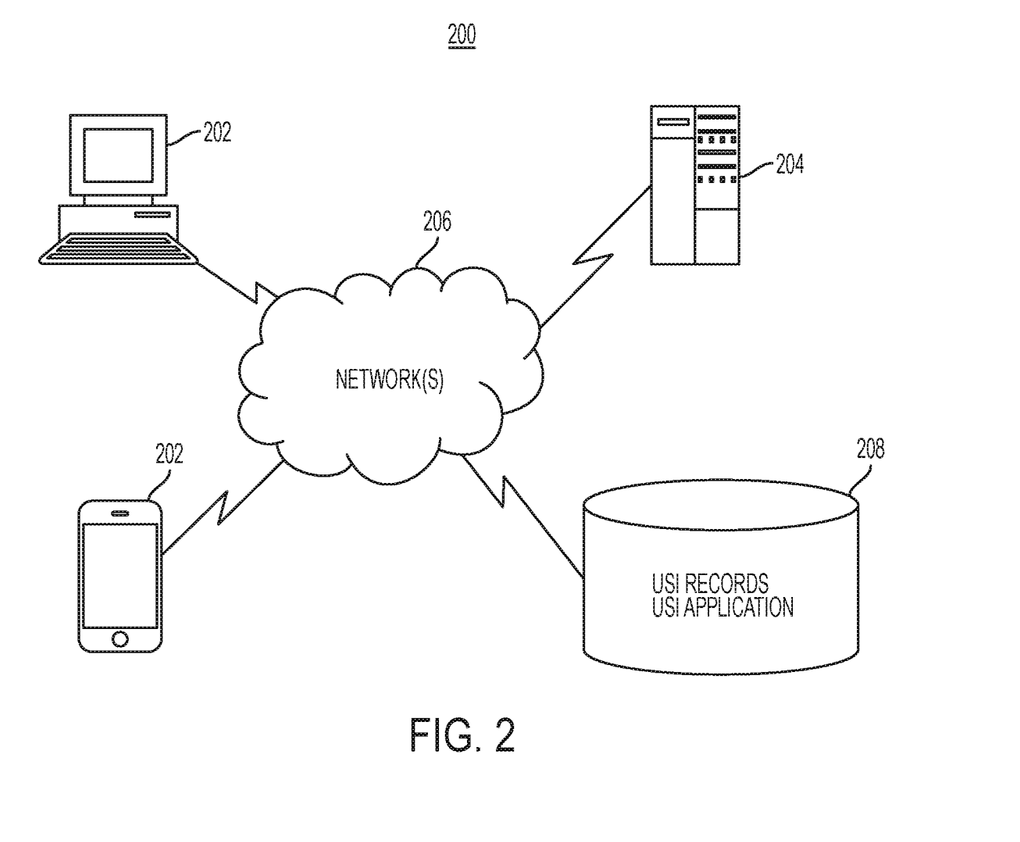
FIG. 2 illustrates a system upon which universal subscriber identity recognition and data classification can be implemented according to an embodiment.

Turning now to FIG. 2, a system 200 in which the universal subscriber identification service may be implemented will now be described in an embodiment. The system 200 includes user devices 202, host system computer 204, and storage device 208, each of which is communicatively coupled to one or more networks 206. The user devices 202 represent end user communications devices, implemented by subscribers of the universal subscriber identification service, and may be implemented as a personal computer (e.g., desktop computer) or mobile device, such as a smart phone, as shown in FIG. 2. In addition, other user devices may be employed to realize the advantages of the embodiments described herein. For example, consumer or home appliances, building or home security network devices, vehicle control system devices, etc., may be used in implementing the universal subscriber identification service described herein.

The host system computer 204 may be a high-speed processing device capable of handling the volume of activities conducted between subscribers of the universal subscriber identification service and the host system computer 204. In an embodiment, the host system computer 204 is implemented by a service provider enterprise of the universal subscriber identification service. As indicated above the universal subscriber identification service may be implemented in a client/server architecture or as part of a cloud computing infrastructure.

The storage device 208 stores universal subscriber identification service records of subscribers, as well as one or more applications (referred to herein as universal subscriber identification service application) for implementing the exemplary processes described herein. The storage device 208 may be implemented using a variety of devices for storing electronic information. It is understood that the storage device 208 may implemented using memory contained in the host system computer 204 or it may be a separate physical device, as illustrated in FIG. 2. The storage device 208 may be logically addressable as a consolidated data source across a distributed environment that includes one or more networks, such as networks 206. Information stored in the storage device 208 is retrieved and manipulated via the host system computer 204, as well as by subscribers of the universal subscriber identification service. In an embodiment, the storage device 208 stores information from database 104 described in FIG. 1.

The networks 206 may be any type of known networks including, but not limited to, a wide area network (WAN), a local area network (LAN), a global network (e.g. Internet), a virtual private network (VPN), and an intranet. The networks 206 may be implemented using wireless networks or any kind of physical network implementation known in the art, e.g., using cellular, satellite, and/or terrestrial networks technologies. The networks 206 may also include short range wireless networks utilizing, e.g., BLUETOOTH™ and WI-FI™ technologies and protocols.

Figure 3:
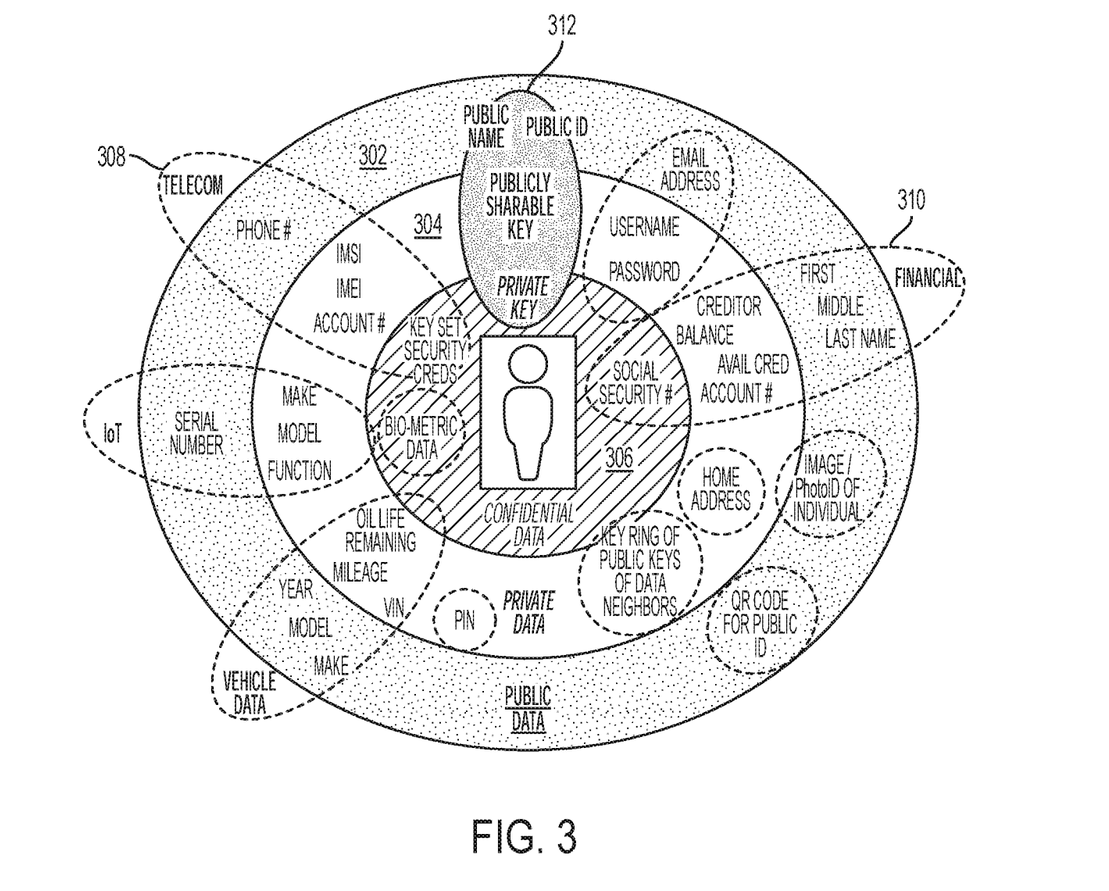
FIG. 3 illustrates a model with sample data elements and subscriber-assigned security levels for use in implementing universal subscriber identity recognition and data classification according to an embodiment.

Turning now to FIG. 3, a model 300 including sample data elements and assigned security levels for a subscriber will now be described in an embodiment. As shown in FIG. 3, and by way of a non-limiting example, the model 300 includes three layers of security, each of which corresponds to a different level of security: public layer 302, private layer 304, and confidential layer 306. These levels are assigned to various data elements stored in a storage space allocated for the subscriber. In an embodiment, the model 300 may be stored in a corresponding record of the subscriber in the storage device 208.

As shown in FIG. 3, a subscriber associated with the model 300 has assigned a security level of 'public' to data elements, such as first, middle, and last name; email address; and phone number; as indicated in the layer 302. Also, as shown in FIG. 3, the subscriber may group certain data elements that share some relationship under a general category. In the model 300, the subscriber groups data elements, such as phone number, International Mobile Subscriber Identity (IMSI), International Mobile Station Equipment Identity (IMEI), account number, key set, and security credentials, as a single data set under the category "Telecom" 308. In another example, the subscriber has grouped data elements, such as name, creditor, balance, available credit, account number, and social security as another data set under another category "Financial" 310. Each level of security beginning from the outer layer 302 and moving inward has increased access protection schemes assigned to corresponding data elements. In the case of grouped data elements, such as Telecom 308, it can be seen that different data elements from the same data set can have different access protection schemes assigned thereto. In an embodiment, a data element grouping (data set) having data elements spanning multiple security levels can be shared with another individual or entity, e.g., by applying a single access protection scheme to all of the data elements in the data set, whereby the single access protection scheme reflects the highest security level associated with any data element in the data set. In another embodiment, the data elements of a data set can be shared individually, whereby each data element is configured with an access protection scheme corresponding to its current security level.

In an embodiment, the model 300 also includes a data set 312 that includes a public identifier, which identifies the particular subscriber and differentiates the subscriber from other subscribers in the system. The data set 312 also includes a public key assigned to the subscriber, as well as a private key assigned to the subscriber. The subscriber's assignment of security levels to the data elements governs the way these keys are used in protecting the exchange of the data elements.

In an embodiment, a subscriber and/or public individual or entity may freely access data elements in the layer 302. In other words, no access protection scheme is applied to these data elements. In addition, a subscriber and/or public individual or entity may access data elements in the layer 304 under an access protection scheme defined for that layer 304. In an embodiment, the access protection scheme for layer 304 may include using the subscriber's private key to encrypt the data elements, and a security envelope containing the encrypted data elements are sent to another subscriber who has been authorized by the subscriber to receive the data elements. If the target recipient of the security envelope possesses a shared public key with the sending subscriber, then the security envelope may contain only the encrypted data elements. However, if the target recipient does not possess a shared public key with the sending subscriber (e.g., the target recipient is not a subscriber of the universal subscriber identification service), the security envelope may contain the public key for decrypting the data elements.

In a further embodiment, a subscriber and/or public individual or entity may access data elements in the layer 306 under an access protection scheme defined for that layer 306. In an embodiment, the access protection scheme for layer 306 may include using the subscriber's private key to digitally sign the data elements, followed by using the public key of the target recipient to encrypt the data elements, such that only the intended recipient can access the security envelope.

Figure 4:
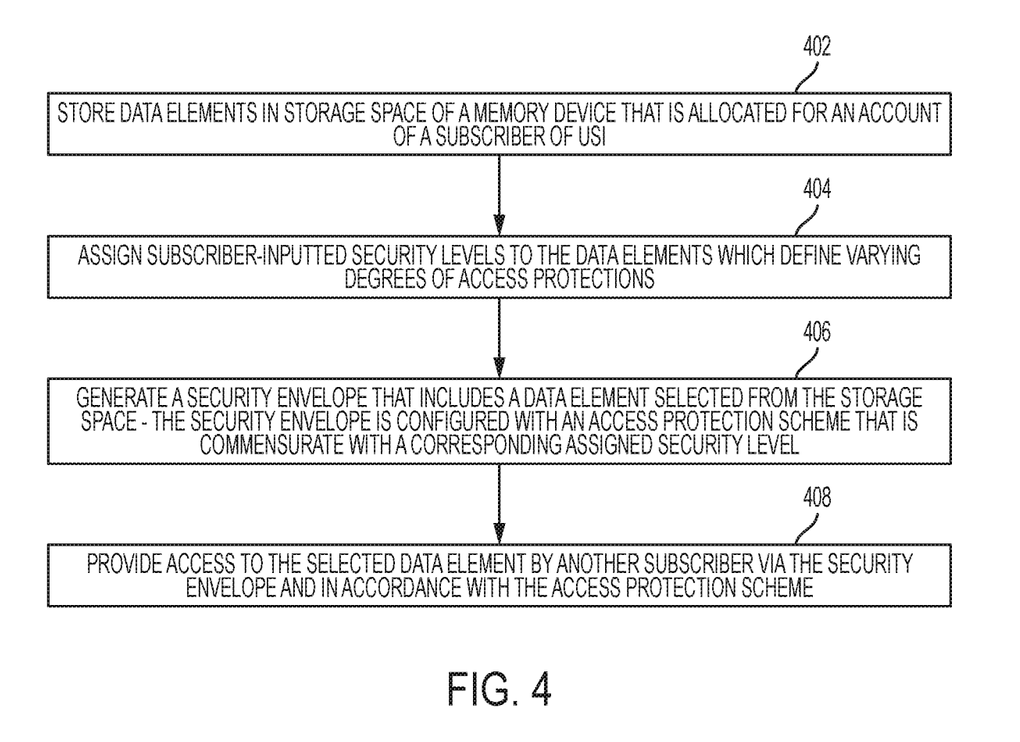
FIG. 4 illustrates a flow diagram for implementing universal subscriber identity recognition and data classification according to an embodiment.

Turning now to FIG. 4, a flow diagram describing a process for implementing the universal subscriber identification service will now be described in an embodiment. The process may be implemented via the universal subscriber identification service application in storage device 208 of FIG. 2. Blocks 402-404 are directed to setting up the data elements through a subscriber account and assigning security levels to the data elements by the subscriber. Blocks 406 and 408 are directed to handling the sharing of the data elements based on the assigned access levels.

In block 402, the data elements for a subscriber are stored in a storage space allocated for an account of the subscriber of the universal subscriber identification service. In block 404, subscriber-inputted security levels are assigned to the data elements. As indicated above, the security levels define varying degrees of access protections associated with the data elements.

When the subscriber desires to share a data element, or alternatively, if another subscriber or individual requests a certain data element, a security envelope is generated in block 406 that includes the data element. The security envelope is configured with an access protection scheme that is commensurate with a corresponding assigned security level. For example, if the data element is the subscriber's social security number, an access protection scheme corresponding to layer 306 is applied in generating the security envelope.

In block 408, access to the data element is provided to the other subscriber or recipient via the security envelope.

Figure 5:
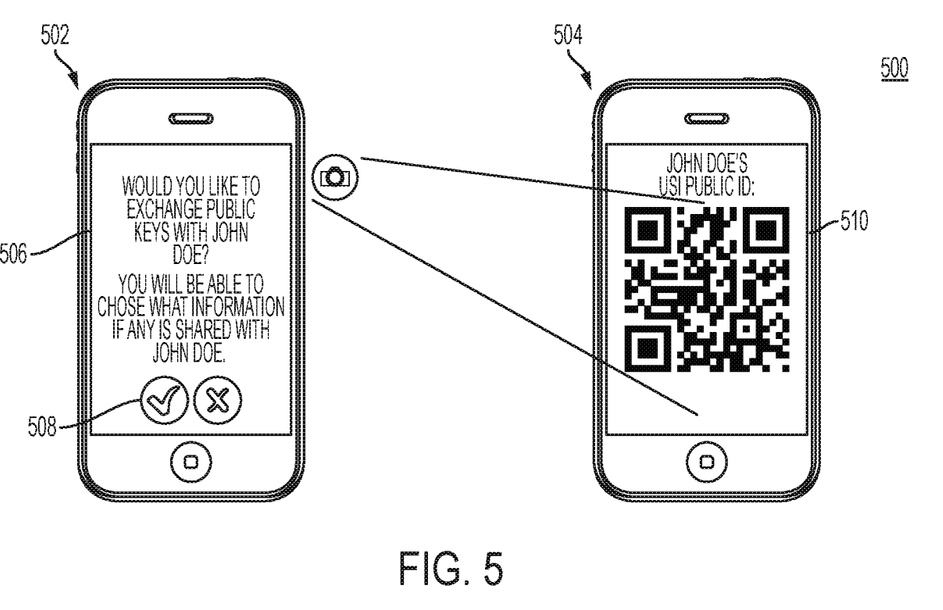
FIG. 5 is an example scenario in which the universal subscriber identity recognition and data classification can be implemented according to an embodiment.

Turning now to FIG. 5, an example scenario 500 in which the universal subscriber identification service may be implemented will now be described in an embodiment. In the example of FIG. 5, two individuals may be in close proximity of one another, such that one individual's device 502 discovers the presence of another individual's device 504. The presence detection may be facilitated through radio frequency identification (RFID) and/or other short-range communications protocols, such as BLUETOOTH or WI-FI. An interface screen is displayed on the discovering device 502 (e.g., through the interface engine 110 in FIG. 1), which prompts 506 the individual to exchange public keys and public identifier with the discovered device 504. Options 508 for accepting the invitation or rejecting the invitation are also displayed. If the individual accepts the invitation, the individual can capture the discovered device's 504 public key in a variety of ways. As shown in FIG. 5, e.g., the discovering device 502 uses a camera feature to record the discovered device's 504 public key, which is displayed on the discovered device 504 as a quick response (QR) code 510. The discovering device 502 receives the QR code, and the code is decrypted to identify the public key. In this manner, it can be seen that public keys can be exchanged on demand and directly between individuals in a peer-to-peer (P2P) exchange. This is also shown generally in FIG. 1 as 112. In this embodiment, the discovered device 504 can now access data elements from the subscriber of discovering device 502 based on the access permissions associated with the public key.

Figure 6:
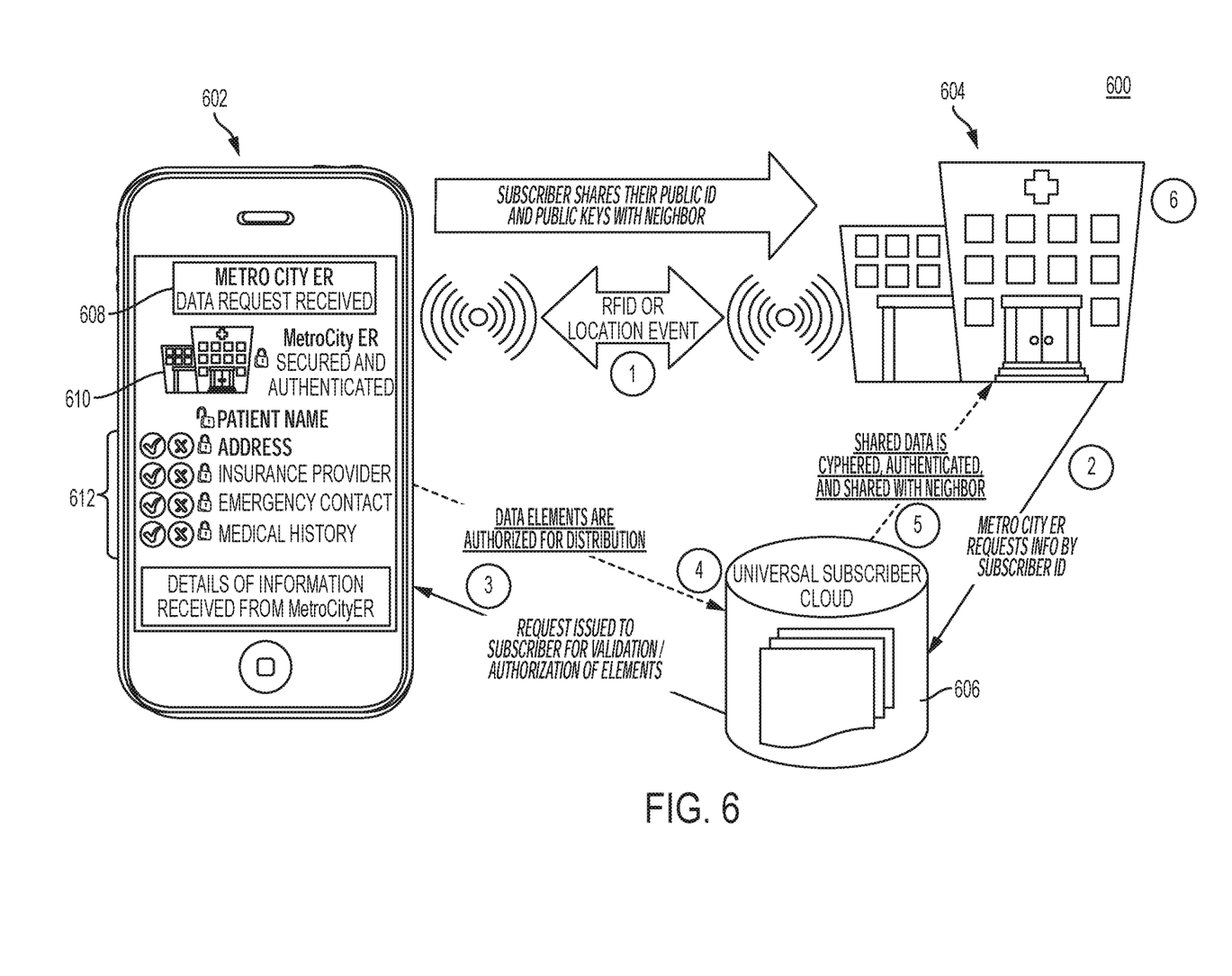
FIG. 6 is another example scenario in which the universal subscriber identity recognition and data classification can be implemented according to an embodiment.

Turning now to FIG. 6, another example scenario 600 in which the universal subscriber identification service may be implemented will now be described in an embodiment. FIG. 6 illustrates a user device 602, which is a communications device (e.g., 202) of a subscriber of the universal subscriber identification service. It is assumed for purposes of the scenario of FIG. 6 that the subscriber has entered a medical facility 604. The medical facility 604 may also be a subscriber of the universal subscriber identification service. The facility 604 may have network capabilities, such that the discovery of the subscriber's device 602 is detected at the facility through a short-range wireless network. Since the subscriber's public identifier is freely accessible to the public, the medical facility 604 can readily identify the subscriber from the subscriber's identifier, which may be determined from communication exchange. The exchange between the device 602 and the medical facility 604 can also include transmission of the public key of the subscriber to the medical facility 604. This exchange is shown as Step 1 in FIG. 6.

Using the public key of the subscriber, the medical facility 604 sends a request to the universal subscriber identification service system 606 (e.g., host system computer 204 and storage device 208) for information about the subscriber (Step 2). The host system computer 204 in turn sends a request to the subscriber (e.g., via the user device 602) to validate or authorize the release of the information requested by the medical facility 604 (Step 3). As shown in FIG. 6, the user device 602 includes an interface (e.g., via the interface engine 110 of FIG. 1) that identifies the medical facility requesting the information (608), an authentication status of the medical facility 604 (610), and a listing of the information (e.g., data elements) requested by the medical facility (612) along with corresponding options to approve or reject the release of the individual data elements. If the individual authorizes the release of the requested information, an authorization message is transmitted by the device 602 to the universal subscriber identification service system 606 (Step 4). The universal subscriber identification service system 606 retrieves the data elements from storage and determines the security levels assigned to the data elements by the subscriber. The universal subscriber identification service system 606 then generates a security envelope of the data elements and sends the information to the medical facility (Step 5). The medical facility uses the public key to decrypt the data elements (Step 6).

In an embodiment, the subscriber need not be an individual but might be a device. For example, using the medical example scenario 600 above, devices within the medical facility (e.g., an MRI device) can be a subscriber with its own unique identifier and subscriber record (e.g., a subscriber record including data elements with assigned security levels similar to those shown in model 300). In addition, a facility such as the medical facility can be a primary subscriber that has multiple subscribers within the facility 604 that are associated with the primary subscriber. These multiple subscribers in turn can be individuals, such as doctors, therapists, lab techs, etc. Also, the multiple subscribers can be departments within the medical facility 604, such as billing, patient registration, emergency room, etc. In addition, the multiple subscribers can be medical machinery or testing devices. In this embodiment, the access scheme applied to various patient-related data elements can be applied more granularly, such that, e.g., one data element can be shared with all of the multiple subscribers associated with the medical facility, while another data element may only be shared with the patient's doctor. In addition, data elements resulting from medical testing (e.g., a subscribing MRI device) with respect to the subscriber may be stored as a data element in the subscriber's record and shared with the subscriber, the subscriber's doctor, and/or another authorized entity (e.g., a specialist outside of the medical facility 604).

In an embodiment, the universal subscriber identification service records may store instances of data access and sharing between the subscriber and other individuals or entities. For example, each time a data element is shared, the subscriber record may store the identity of a recipient of the data element, a means of transmission of the data element (e.g., direct P2P exchange, through a particular subscriber communications device, etc.), and a validity period that identifies a period of time in which the security envelope may be accessed by a recipient. The subscriber may define the validity period, e.g., through the data and rule set engine 108 of FIG. 1, or may be defined on an ad hoc basis in which the validity period is defined for a particular data element exchange. Through this tracking, the subscriber can review who has been given access to which data elements of the subscriber, as well as when the access occurred. Over time, this information can be helpful in understanding whether, if any, security issues may have occurred. For example, if the user's financial account data has been exposed, the subscriber can view a snapshot of who received this data and when. The subscriber can then adjust the security levels for various data elements, as well as the permissions granted to other individuals in order to minimize any risks.

As described above, the exemplary embodiments can be in the form of processor-implemented processes and devices for practicing those processes, such as processor. The exemplary embodiments can also be in the form of computer program code containing instructions embodied in tangible media, such as floppy diskettes, CD ROMs, hard drives, or any other computer-readable storage medium, wherein, when the computer program code is loaded into and executed by a computer, the computer becomes a device for practicing the exemplary embodiments. The exemplary embodiments can also be in the form of computer program code, for example, whether stored in a storage medium, loaded into and/or executed by a computer, or transmitted over some transmission medium, loaded into and/or executed by a computer, or transmitted over some transmission medium, such as over electrical wiring or cabling, through fiber optics, or via electromagnetic radiation, wherein, when the computer program code is loaded into an executed by a computer, the computer becomes an device for practicing the exemplary embodiments. When implemented on a general-purpose microprocessor, the computer program code segments configure the microprocessor to create specific logic circuits.

While the invention has been described with reference to exemplary embodiments, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiments disclosed for carrying out this invention, but that the invention will include all embodiments falling within the scope of the claims. Moreover, the use of the terms first, second, etc., do not denote any order or importance, but rather the terms first, second, etc., are used to distinguish one element from another. Furthermore, the use of the terms a, an, etc., do not denote a limitation of quantity, but rather denote the presence of at least one of the referenced item.

What is claimed is:

1. A method comprising:
assigning, via a computer processor, one or more subscriber-inputted security levels to at least a portion of data elements stored in a storage space of a memory device, the storage space allocated for an account of a subscriber of a subscriber identification system, the one or more subscriber-inputted security levels having been input by the subscriber; and
providing, via the computer processor, access to the at least the portion of the data elements in the storage space of the memory device by another subscriber according to the one or more subscriber-inputted security levels assigned to the at least the portion of the data elements;
wherein any of the data elements having no subscriber-inputted security levels assigned are inaccessible to any other subscriber but the subscriber.

2. The method of claim 1, wherein the one or more subscriber-inputted security levels define varying degrees of access protections associated with the at least the portion of the data elements.

3. The method of claim 1, further comprising generating, via the computer processor, a security envelope that includes at least one selected data element of the at least the portion of the data elements in the storage space;
wherein the security envelope is configured with an access protection scheme that is commensurate with the one or more subscriber-inputted security levels assigned for the at least one selected data element.

4. The method of claim 3, wherein providing, via the computer processor, access to the at least one selected data element by the another subscriber according to the one or more subscriber-inputted security levels comprises providing the security envelope to the another subscriber in accordance with the access protection scheme.

5. The method of claim 3, wherein the access protection scheme includes shared public key encryption and decryption between the subscriber as a sender of the security envelope and the another subscriber as a recipient of the security envelope.

6. The method of claim 3, wherein the access protection scheme includes encrypting the at least one selected data element with a public key of the another subscriber as a recipient and signing with a public key of the subscriber as a sender.

7. The method of claim 3, wherein the access protection scheme includes encrypting and authenticating the at least one selected data element with both a public key of the subscriber and a public key of a sender.

8. The method of claim 1, further comprising grouping related data elements of the at least the portion of the data elements into data sets for a plurality of subject categories, wherein at least one data element in a data set of the data sets within a subject category is assigned to a particular one of the one or more subscriber-inputted security levels that is different than another particular one of the one or more subscriber-inputted security levels assigned to another data element in the data set.

9. The method of claim 1, wherein some of the data elements that are not encrypted in the storage space are publicly accessible to other subscribers of the subscriber identification system, the some of the data elements being publicly accessible are retrieved via a public identifier assigned to the subscriber of the account.

10. The method of claim 1, wherein the data elements include medical data associated with the subscriber as a patient and the another subscriber is a medical facility, the method further comprising:
receiving a request from the medical facility to access the medical data stored in the storage space, the request generated in response to identification of the subscriber at the medical facility;
sending a prompt to a communications device of the subscriber to authorize the access of the medical data by the medical facility; and
sending the medical data via a security envelope to the medical facility in response to authorization given by the subscriber, the security envelope configured with an access protection scheme associated with a corresponding assigned subscriber-inputted security level assigned to the medical data.

11. An apparatus, comprising:
a processor; and
memory comprising computer-executable instructions that, when executed by the processor, cause the processor to perform operations, the operations comprising:
assigning one or more subscriber-inputted security levels to at least a portion of data elements stored in a storage space of the memory, the storage space allocated for an account of a subscriber of a subscriber identification system, the one or more subscriber-inputted security levels having been input by the subscriber; and
providing access to the at least the portion of the data elements in the storage space of the memory by another subscriber according to the one or more subscriber-inputted security levels assigned to the at least the portion of the data elements;
wherein any of the data elements having no subscriber-inputted security levels assigned are inaccessible to any other subscriber but the subscriber.

12. The apparatus of claim 11, wherein the one or more subscriber-inputted security levels define varying degrees of access protections associated with the at least the portion of the data elements.

13. The apparatus of claim 11, wherein the operations further comprise generating, via the processor, a security envelope that includes at least one selected data element of the at least the portion of the data elements in the storage space; and
wherein the security envelope is configured with an access protection scheme that is commensurate with the one or more subscriber-inputted security levels assigned for the at least one selected data element.

14. The apparatus of claim 13, wherein providing access to the at least one selected data element by the another subscriber according to the one or more subscriber-inputted security levels comprises providing the security envelope to the another subscriber in accordance with the access protection scheme.

15. The apparatus of claim 13, wherein the access protection scheme includes shared public key encryption and decryption between the subscriber as a sender of the security envelope and the another subscriber as a recipient of the security envelope.

16. The apparatus of claim 13, wherein the access protection scheme includes encrypting the at least one selected data element with a public key of the another subscriber as a recipient and signing with a public key of the subscriber as a sender.

17. The apparatus of claim 13, wherein the access protection scheme includes encrypting and authenticating the at least one selected data element with both a public key of the subscriber and a public key of a sender.

18. A computer program product comprising a non-transitory computer readable medium, the computer program product including instructions that, when executed by a processor, cause the processor to perform operations comprising:

assigning, via the processor, one or more subscriber-inputted security levels to at least a portion of data elements stored in a storage space of a memory device, the storage space allocated for an account of a subscriber of a subscriber identification system, the one or more subscriber-inputted security levels having been input by the subscriber; and providing, via the processor, access to the at least the portion of the data elements in the storage space of the memory device by another subscriber according to the one or more subscriber-inputted security levels assigned to the at least the portion of the data elements;

wherein any of the data elements having no subscriber-inputted security levels assigned are inaccessible to any other subscriber but the subscriber.

\* \* \* \* \*